US00PP15397P2

(12) United States Plant Patent
Wood

(10) Patent No.: US PP15,397 P2
(45) Date of Patent: Dec. 7, 2004

(54) ***SPIRAEA* PLANT NAMED 'WILMA'**

(50) Latin Name: *Spiraea fritschiana*
Varietal Denomination: Wilma

(75) Inventor: Timothy D. Wood, Grand Haven, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 196 days.

(21) Appl. No.: 10/232,890

(22) Filed: Aug. 31, 2002

(51) Int. Cl.[7] ..... A01H 5/00
(52) U.S. Cl. ..... Plt./226
(58) Field of Search ..... Plt./226, 263

*Primary Examiner*—Howard J. Locker
(74) *Attorney, Agent, or Firm*—C. A. Whealy

(57) ABSTRACT

A distinct cultivar of *Spiraea* plant named 'Wilma', characterized by its upright and rounded plant habit; freely branching growth habit; red-colored young leaves; freely flowering habit; vibrant pink-colored flowers; and excellent garden performance.

1 Drawing Sheet

Botanical classification/cultivar designation: *Spiraea fritschiana* cultivar Wilma.

BACKGROUND OF THE INVENTION

The present Invention relates to a new and distinct cultivar of *Spiraea* plant, botanically known as *Spiraea fritschiana*, and hereinafter referred to by the cultivar name Wilma.

The new *Spiraea* originated from a cross-pollination during the spring of 1995 of two unidentified selections of *Spiraea fritschiana*, not patented. The cultivar Wilma was discovered and selected by the Inventor as a single plant within the progeny of the stated cross-pollination in a controlled environment in East Lansing, Mich. The selection of the new *Spiraea* was based on its vibrant pink-colored flowers.

Asexual reproduction of the new cultivar by softwood cuttings taken at Grand Haven, Mich., since spring, 1997, has shown that the unique features of this new *Spiraea* are stable and reproduced true to type in successive generations.

SUMMARY OF THE INVENTION

Plants of the cultivar Wilma have not been observed under all possible environmental conditions. The phenotype may vary somewhat with variations in environment such as temperature and light intensity without, however, any variance in genotype.

The following traits have been repeatedly observed and are determined to be the unique characteristics of 'Wilma'. These characteristics in combination distinguish 'Wilma' as a new and distinct cultivar:

1. Upright and rounded plant habit.
2. Freely branching growth habit.
3. Red-colored young leaves.
4. Freely flowering habit.
5. Vibrant pink-colored flowers.
6. Excellent garden performance.

Plants of the new *Spiraea* are most similar to the parent selections and differ from plants of parent selections and other known selections of *Spiraea fritschiana* in the following characteristics:

1. Plants of the new *Spiraea* are more freely branching than other known selections of *Spiraea fritschiana.*
2. Young leaves of plants of the new *Spiraea* are more red in color than young leaves of other known selections of *Spiraea fritschiana.*
3. Plants of the new *Spiraea* have larger inflorescences with more flowers per inflorescence than other known selections of *Spiraea fritschiana.*
4. Plants of the new *Spiraea* have pink-colored flowers whereas other known selections of *Spiraea fritschiana* have white-colored flowers.

BRIEF DESCRIPTION OF THE PHOTOGRAPHS

The accompanying colored photographs illustrate the unique appearance of the new cultivar, showing the colors as true as it is reasonably possible to obtain in colored reproductions of this type. Colors in the photographs may differ from the color values cited in the detailed botanical description which accurately describe the colors of the new *Spiraea.*

The photograph at the top of the sheet comprises a side perspective view of a typical plant of 'Wilma' grown in the landscape.

The photograph at the bottom of the sheet is a close-up view of inflorescences of a typical plant of 'Wilma'.

DETAILED BOTANICAL DESCRIPTION

In the following description, color references are made to The Royal Horticultural Society Colour Chart, 1995 Edition, except where general terms of ordinary dictionary significance are used. Plants used in the aforementioned photographs and in the following description were grown in Grand Haven, Mich., in ground beds in an outdoor nursery and under conditions which closely approximate commercial production conditions. Plants were about two years old when the photographs and description were taken. The photographs and description were taken during the summer.

Botanical classification: *Spiraea fritschiana* cultivar Wilma.
Parentage:

*Male, or pollen, parent.*—Unidentified *Spiraea fritschiana* selection, not patented.

*Female, or seed, parent.*—Unidentified *Spiraea fritschiana* selection, not patented.

Propagation:

*Type cutting.*—By softwood cuttings.

*Time to initiate roots.*—About 15 days at 21° C.

*Time to produce a rooted cutting or liner.*—About 60 days at 21° C.

*Root description.*—Fine, fibrous.

*Rooting habit.*—Freely branching.

Plant description:

*Form/growth habit.*—Upright and rounded plant habit; bushy perennial shrub.

*Usage.*—Appropriate for one to three-gallon containers.

*Plant height, soil level to top of plant plane.*—About 76 cm.

*Plant diameter or area of spread.*—About 90 cm.

*Branching habit.*—When pinched, freely branching with potentially about 108 lateral branches per plant.

*Lateral branches.*—Length: About 20 cm. Diameter: About 3 to 4 mm. Internode length: About 2 cm. Texture: Glabrous. Color: 143C.

*Foliage description.*—Arrangement: Alternate, simple. Quantity per laterla branch: Typically about 17. Length: About 4 cm. Width: About 2.5 cm. Shape: Ovate. Apex: Acute. Base: Acute to obtuse. Margin: Serrate. Texture: Upper surface: Glabrous. Lower surface: Slightly pubescent. Venation pattern: Pinnate. Color: Young foliage, upper and lower surfaces: 181A. Mature foliage, upper surface: 146B. Mature foliage, lower surface: 146C. Venation, upper surface: Midrib, 144A; lateral veins, 146C. Venation, lower surface: All veins, 144A. Petiole: Length: About 2 mm. Diameter: About 1 mm. Color: 144A.

Flower description:

*Flower type and habit.*—Single rotate flowers arranged on terminal corymbs; corymbs hemispherical. Flowers not persistent. Flowers not fragrant.

*Natural flowering season.*—Continuously flowering from early to mid-June in Grand Haven, Mich.

*Flower longevity.*—Flowers last about three to four weeks on the plant.

*Quantity of flowers.*—Freely flowering, about 153 flowers per inflorescence.

*Corymb diameter.*—About 10 cm.

*Corymb height.*—About 8 cm.

*Flower diameter.*—About 6 mm.

*Flower depth (height).*—About 9 mm.

*Flower buds.*—Length: About 1 mm. Diameter: About 1 mm. Shape: Spherical. Color: 186C.

*Petals.*—Quantity per flower: About five. Length: About 2.5 mm. Width: About 2.5 mm. Shape: Rounded. Apex: Obtuse. Base: Obtuse. Margin: Entire. Texture, upper and lower surfaces: Smooth, glabrous. Color: When opening, upper and lower surfaces: 186D. Fully opened, upper and lower surfaces: 186D.

*Sepals.*—Quantity per flower: About five. Length: About 1 mm. Width: Less than 1 mm. Shape: Ovate. Apex: Acute. Base: Attenuate. Margin: Entire. Texture, upper and lower surfaces: Smooth, glabrous. Color, upper and lower surfaces: 147D.

*Pedicels.*—Angle: About 20 to 45° from vertical. Strength: Moderately strong. Length: About 2 to 3 mm. Color: 147D.

*Reproductive organs.*—Stamens: Quantity per flower: About 15. Anther shape: Filiform. Anther length: About 2.5 mm. Anther color: 186D. Pollen amount: Scarce. Pollen color: 57A. Pistils: Pistil quantity per flower: Five. Pistil length: About 1 mm. Stigma shape: Rounded. Stigma color: 186D. Style length: About 1 mm. Style color: 186D. Ovary color: 145B. Seed: Length: Less than 0.5 mm. Diameter: Less than 0.5 mm. Color: Close to 166A.

Disease/pest resistance: Under commercial production conditions, plants of the new *Spiraea* have not been observed to be resistant to pathogens or pests common to *Spiraea*.

Weather tolerance: Plants of the new *Spiraea* have been shown to be tolerant to temperatures ranging from −30 to 35° C. Flowers of plants have exhibited excellent tolerance to wind and rain.

It is claimed:

1. A new and distinct cultivar of *Spiraea* plant named 'Wilma', as illustrated and described.

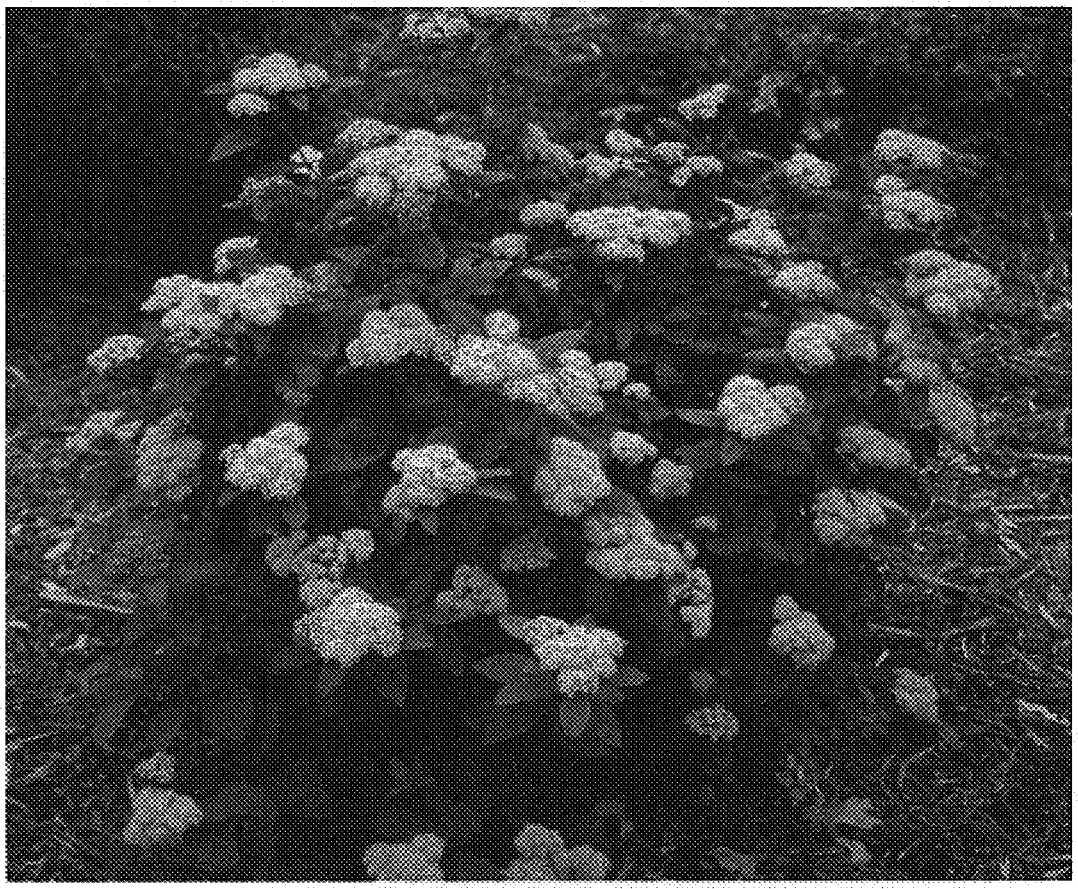
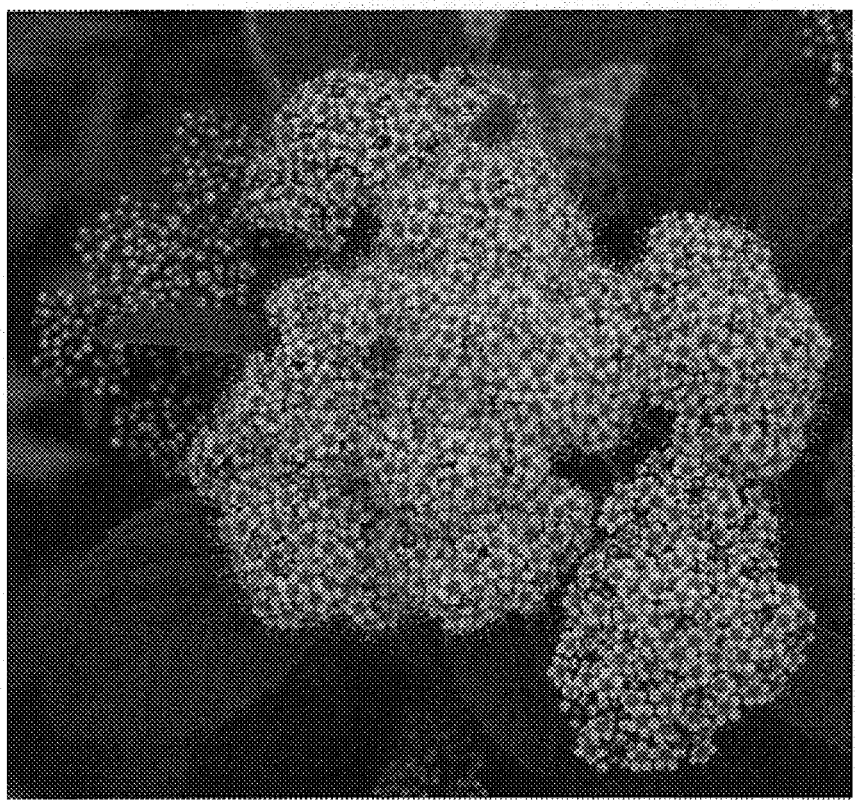

* * * * *